US008895762B2

(12) United States Patent
Horns et al.

(10) Patent No.: US 8,895,762 B2
(45) Date of Patent: Nov. 25, 2014

(54) PROCESS FOR THE PREPARATION OF SULFAMIDE DERIVATIVES

(71) Applicant: Janssen Pharmaceutica NV, Beerse (BE)

(72) Inventors: Stefan Horns, Schaffhausen (CH); Roger Faessler, Stetten (CH)

(73) Assignee: Janssen Pharmaceutica NV, Beerse (BE)

( * ) Notice: Subject to any disclaimer, the term of this patent is extended or adjusted under 35 U.S.C. 154(b) by 77 days.

(21) Appl. No.: 13/630,142

(22) Filed: Sep. 28, 2012

(65) Prior Publication Data

US 2013/0085175 A1   Apr. 4, 2013

Related U.S. Application Data

(60) Provisional application No. 61/540,800, filed on Sep. 29, 2011.

(51) Int. Cl.
*C07D 319/14* (2006.01)
*C07D 319/20* (2006.01)

(52) U.S. Cl.
CPC .................................. *C07D 319/20* (2013.01)
USPC ........................................................ 549/362

(58) Field of Classification Search
USPC ........................................................ 549/362
See application file for complete search history.

(56) References Cited

U.S. PATENT DOCUMENTS

| | | |
|---|---|---|
| 2006/0041008 A1 | 2/2006 | McComsey et al. |
| 2007/0155821 A1 | 7/2007 | Smith-Swintosky et al. |
| 2007/0155822 A1 | 7/2007 | Smith-Swintosky et al. |
| 2007/0155823 A1 | 7/2007 | Smith-Swintosky et al. |
| 2007/0155824 A1 | 7/2007 | Smith-Swintosky et al. |
| 2007/0155825 A1 | 7/2007 | Smith-Swintosky |
| 2007/0155826 A1 | 7/2007 | Smith-Swintosky et al. |
| 2007/0155827 A1 | 7/2007 | Smith-Swintosky et al. |
| 2007/0191474 A1 | 8/2007 | Smith-Swintosky |
| 2007/0293440 A1 | 12/2007 | Smith-Swintosky et al. |
| 2008/0027131 A1 | 1/2008 | Smith-Swintosky et al. |
| 2009/0247616 A1 | 10/2009 | Smith-Swintosky |
| 2009/0247617 A1 | 10/2009 | Abdel-Magid et al. |
| 2009/0247618 A1 | 10/2009 | Ballentine et al. |
| 2009/0318544 A1 | 12/2009 | Mehrman et al. |

FOREIGN PATENT DOCUMENTS

WO   WO 2009/120192   10/2009

OTHER PUBLICATIONS

International Search Report re: PCT/EP2012/069293 dated Nov. 12, 2012.

*Primary Examiner* — Andrew D Kosar
*Assistant Examiner* — Raymond Covington
(74) *Attorney, Agent, or Firm* — Hal B. Woodrow

(57) ABSTRACT

The present invention is directed to an improved process for the preparation of sulfamide derivatives.

9 Claims, No Drawings

PROCESS FOR THE PREPARATION OF SULFAMIDE DERIVATIVES

CROSS REFERENCE TO RELATED APPLICATIONS

This application claims the benefit of U.S. Provisional Application 61/540,800, filed on Sep. 29, 2011, which is incorporated by reference herein in its entirety.

FIELD OF THE INVENTION

The present invention is directed to an improved process for the preparation of sulfamide derivatives.

BACKGROUND OF THE INVENTION

McComsey, D., et al., in US Patent Publication 2006/0041008 A1, published Feb. 23, 2006 disclose sulfamide derivatives of the following formula

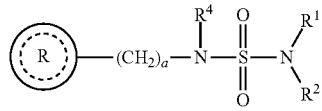

useful for the treatment of epilepsy and related disorders. McComsey et al., further disclose a process for the preparation of sulfamide derivatives, including the process shown below

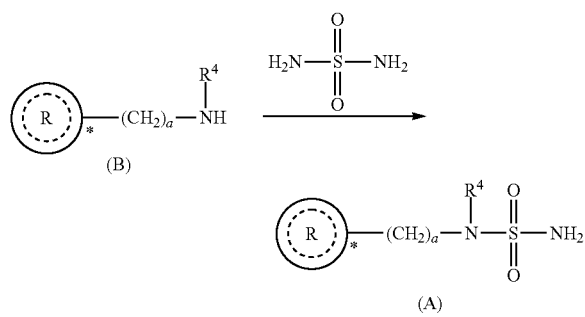

where a compound of formula (B) is reacted with sulfamide; in an organic solvent such as THF, dioxane, and the like; preferably at an elevated temperature in the range of about 50° C. to about 100° C., more preferably at about reflux temperature; to yield the corresponding compound of formula (A).

Abdel-Magid, A., et al., in US Patent Publication 2009/0247617 A1, Sep. 26, 2009 disclose a process for the preparation of sulfamide derivatives, as shown below

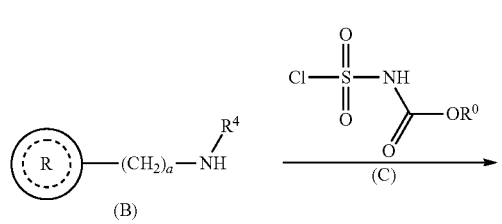

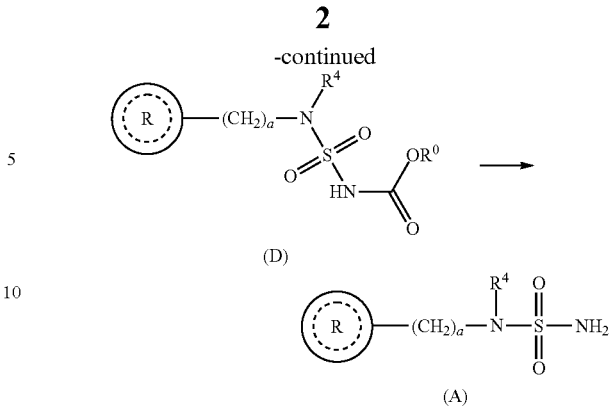

where a suitably substituted compound of formula (B), is reacted with a nitrogen protected compound of formula (C) (wherein —C(O)OR⁰ is a nitrogen protecting group, for example, an alkoxycarbonyl, aryloxycarbonyl, aralkyloxycarbonyl, and the like); in the presence of an organic or inorganic base; in an aprotic organic solvent; to yield the intermediate compound of formula (D), which is then deprotected according to known methods to yield the corresponding compound of formula (A).

Ballentine, s., et al., in US Patent Publication 2009/0247618 A1, Sep. 26, 2009 disclose a process for the preparation of sulfamide derivatives as shown below

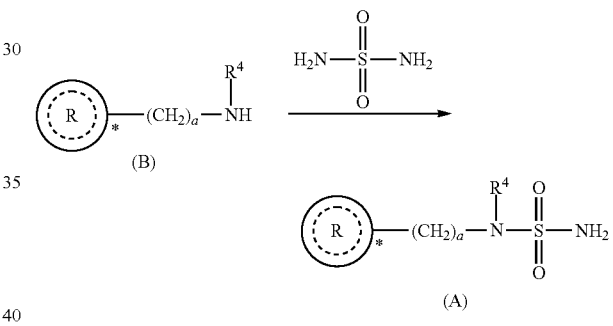

where a suitably substituted compound of formula (B) is reacted with sulfamide; in an organic solvent such as THF, dioxane, and the like; preferably at an elevated temperature in the range of about 50° C. to about 100° C., more preferably at about reflux temperature; to yield the corresponding compound of formula (A).

There remains a need for processes for the preparation of compounds of formula (I), and more particularly the compound of formula (I-S), as hereinafter defined, which are suitably for large scale manufacture.

SUMMARY OF THE INVENTION

The present invention is directed to an improved process for the preparation of compounds of formula (I)

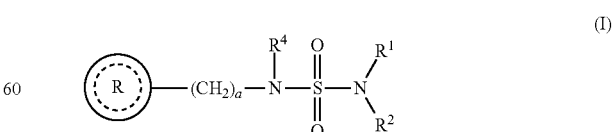

wherein $R^1$ and $R^2$ are each independently selected from the group consisting of hydrogen and lower alkyl; (preferably, $R^1$ and $R^2$ are each hydrogen)

$R^4$ is selected from the group consisting of hydrogen and lower alkyl; (preferably, $R^4$ is hydrogen)

a is an integer from 1 to 2;

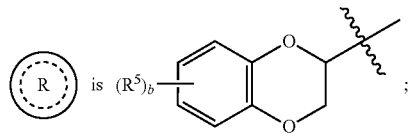

wherein b is an integer from 0 to 4; and wherein each $R^5$ is independently selected from the group consisting of halogen and lower alkyl;

and pharmaceutically acceptable salts thereof;

comprising

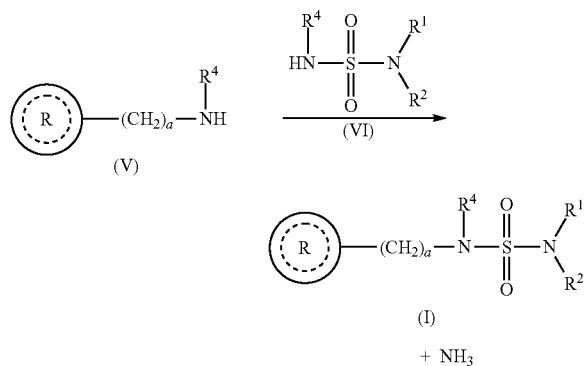

reacting a compound of formula (V) with a compound of formula (VI); in the presence of a buffer system; in water or an aqueous solvent system; at reflux temperature; to yield the corresponding compound of formula (I) and ammonia as a by-product.

In an embodiment, the present invention is directed to an improved process for the preparation of a compound of formula (I-S)

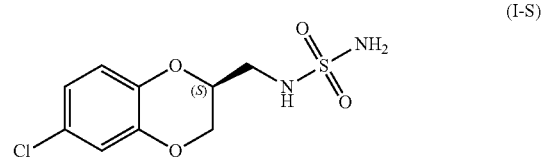

or a pharmaceutically acceptable salt thereof; comprising

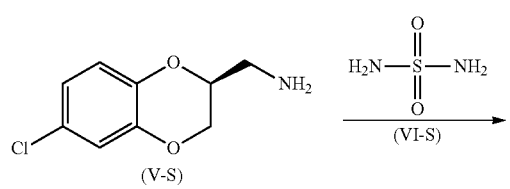

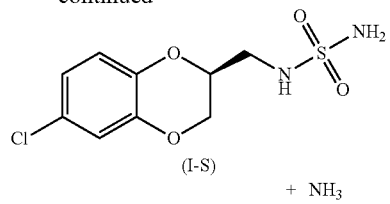

reacting a compound of formula (V-S) with a compound of formula (VI-S); in the presence of a buffer system; in water or an aqueous solvent system; at reflux temperature; to yield the corresponding compound of formula (I-S) and ammonia, as a by-product.

The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating epilepsy or a related disorder comprising administering to a subject in need thereof a therapeutically effective amount of any of the compounds or pharmaceutical compositions described above. Another example of the invention is the use of any of the compounds described herein in the preparation of a medicament for treating epilepsy or a related disorder, in a subject in need thereof. In another example, the present invention is directed to a compound prepared according to a process of the present invention, for use in a methods for treating epilepsy or a related disorder, in a subject in need thereof.

DETAILED DESCRIPTION OF THE INVENTION

The present invention is directed to an improved process for the preparation of compound of formula (I)

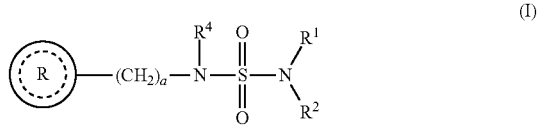

wherein $R^1$, $R^2$, $R^4$, a and

are as herein defined. In an embodiment, the present invention is directed to an improved process for the preparation of a compound of formula (I-S)

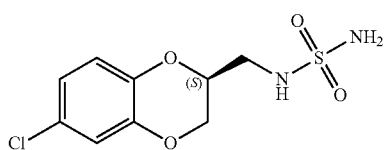

(I-S)

or a pharmaceutically acceptable salt thereof. The compounds of formula (I) are useful in the treatment of epilepsy and related disorders, as disclosed by McComsey et al., in US Patent Publication 2006/0041008 A1, published Feb. 23, 2006.

The present invention is directed to an improved process for the preparation of compounds of formula (I), preferably the compound of formula (I-S), as described in more detail herein.

In one aspect, the process of the present invention comprises the unexpected finding that the coupling reaction (of the compound of formula (V) with the compound of formula (VI), as herein described) may be carried out in water or an aqueous solvent system, preferably at a temperature of about 85° C. to about 90° C. The finding was unexpected, since one of the reactants in the coupling reaction is not highly soluble in water (for example, the solubility of the compound of formula (V-S) in water, at room temperature, is 0.35 g/100 g water). Additionally, the use of a buffering system in the coupling reaction (the use of which would be expected to increase the solubility of the reactant, for example the compound of formula (V-S)) was unexpectedly found to increase the rate of the coupling reaction.

Additionally, the use of water or an aqueous solvent system in the coupling of the compound of formula (V) with the compound of formula (VI) provides one or more of the following additional and/or unexpected benefits, which are particularly advantageous for large scale manufacture of the desired product.

(a) Improved safety and handling: 1,4-Dioxane and other organic solvents present health, safety, handling and/or environments (e.g. disposal) issues, particularly in large manufacturing scale, which are avoided with the use of water or an aqueous solvent system;

(b) Decreased reaction times: As an example, the reaction of the compound of formula (V-S) with the compound of formula (VI-S) was observed to proceed at a faster rate in the water or suitable aqueous solvent system, than in 1,4-dioxane. As a result, the amount of product which may be synthesized in a given time is increased, an advantage which is particularly important in large scale manufacture.

(c) Increased yield: The use of water or an aqueous solvent system allows for azeotropic distillation of the reaction mixture. Azeotropic distillation of the reaction mixture removes ammonia (one of the products of the reaction) from the reaction mixture. As such, the combination of azeotropic distillation and removal of ammonia drives the reaction to preparation of the desired product and therefore to higher overall yields. Additionally, the use of water or an aqueous solvent system allows the reaction to be completed at a temperature of less than or equal to about 90° C., thereby minimizing decomposition of the product (for example, the compound of formula (I-S)).

(d) Improved purity: In for example, the synthesis of the compound of formula (I-S), the use of water or an aqueous solvent system was found to permit isolation of a purer desired product. Since a number of by-products and/or impurities of the process of the present invention are more soluble in water than the desired product, running the coupling reaction in water or an aqueous solvent system results in a mixture wherein the desired product is precipitated out of the mixture and the by-products and/or impurities remain in solution, thereby improving the purity of the isolated product.

In an embodiment, the present invention is directed to a process for the preparation of compounds of formula (I) wherein $R^1$ is selected from the group consisting of hydrogen and methyl. In another embodiment, the present invention is directed to a process for the preparation of compounds of formula (I) wherein $R^2$ is selected from the group consisting of hydrogen and methyl. In yet another embodiment, the present invention is directed to a process for the preparation of compounds of formula (I) wherein $R^1$ and $R^2$ are each hydrogen or $R^1$ and $R^2$ are each methyl.

In an embodiment, the present invention is directed to a process for the preparation of compounds of formula (I) wherein $-(CH_2)_a-$ is selected from the group consisting of $-CH_2-$ and $-CH_2-CH_2-$. In another embodiment, the present invention is directed to a process for the preparation of compounds of formula (I) wherein $-(CH_2)_a-$ is $-CH_2-$.

In an embodiment, the present invention is directed to a process for the preparation of compounds of formula (I) wherein $R^4$ is selected from the group consisting of hydrogen and methyl, preferably, $R^4$ is hydrogen.

In an embodiment, the present invention is directed to a process for the preparation of compounds of formula (I) wherein a is 1.

In an embodiment, the present invention is directed to a process for the preparation of compounds of formula (I) wherein b is an integer from 0 to 2. In another embodiment, the present invention is directed to a process for the preparation of compounds of formula (I) wherein b is an integer from 0 to 1.

In an embodiment, the present invention is directed to a process for the preparation of compounds of formula (I) wherein

is selected from the group consisting of 2-(2,3-dihydro-benzo[1,4]dioxinyl), 2-(6-chloro-2,3-dihydro-benzo[1,4]dioxinyl), 2-(6-fluoro-2,3-dihydro-benzo[1,4]dioxinyl), 2-(5-fluoro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl) and 2-(8-chloro-2,3-dihydro-benzo[1,4]dioxinyl).

In another embodiment, the present invention is directed to a process for the preparation of compounds of formula (I) wherein

is selected from the group consisting 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3- dihydro-benzo[1,4]dioxinyl). In another embodiment, the present invention is directed to a process for the preparation of compounds of formula (I) wherein

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In another embodiment, the present invention is directed to a process for the preparation of compounds of formula (I) wherein

is a ring structure selected from the group consisting of 2-(6-chloro-2,3-dihydro-benzo[1,4]dioxinyl), 2-(5-chloro-2,3-dihydro-benzo[1,4]dioxinyl) and 2-(6,7-dichloro-2,3-dihydro-benzo[1,4]dioxinyl). In another embodiment, the present invention is directed to a process for the preparation of compounds of formula (I) wherein

is a ring structure selected from the group consisting of 2-(5-chloro-2,3-dihydro-benzo[1,4]dioxinyl) and 2-(6,7-dichloro-2,3-dihydro-benzo[1,4]dioxinyl). In another embodiment, the present invention is directed to a process for the preparation of compounds of formula (I) wherein

is 2-(6-chloro-2,3-dihydro-benzo[1,4]dioxinyl).

In an embodiment, the present invention is directed to a process for the preparation of compounds of formula (I) wherein $R^5$ is selected from chloro, fluoro, bromo and methyl. In another embodiment, the present invention is directed to a process for the preparation of compounds of formula (I) wherein $R^5$ is chloro.

In an embodiment, the present invention is directed to a process for the preparation of compounds of formula (I) wherein the stereo-center on the compound of formula (I) is in the S-configuration. In another embodiment, the present invention is directed to a process for the preparation of compounds of formula (I) wherein the stereo-center on the compound of formula (I) is in the R-configuration.

In an embodiment, the present invention is directed to a process for the preparation of compounds of formula (I) wherein the compound of formula (I) is present as an enantiomerically enriched mixture, wherein the % enantiomeric enrichment (% ee) is greater than about 75%, preferably greater than about 90%, more preferably greater than about 95%, most preferably greater than about 98%. In an embodiment, the present invention is directed to a process for the preparation of compounds of formula (I-S) wherein the compound of formula (I-S) is present as an enantiomerically enriched mixture, wherein the % enantiomeric enrichment (% ee) is greater than about 75%, preferably greater than about 90%, more preferably greater than about 95%, most preferably greater than about 98%.

In another embodiment, the present invention is directed to processes for the preparation of any of the representative compounds listed in Table 1 below. In the tables below, the column headed "Stereo" defines the stereo-configuration at the carbon atom of the

group attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | $(CH_2)_a$ | $NR^4$ | $R^1$ | $R^2$ |
|---|---|---|---|---|---|---|
| 1 | 2-(2,3-dihydro-benzo[1,4]dioxinyl) | | $CH_2$ | NH | H | H |
| 4 | 2-(2,3-dihydro-benzo[1,4]dioxinyl) | S | $CH_2$ | NH | H | H |
| 5 | 2-(2,3-dihydro-benzo[1,4]dioxinyl) | R | $CH_2$ | NH | H | H |
| 6 | 2-(2,3-dihydro-benzo[1,4]dioxinyl) | | $CH_2$ | NH | methyl | methyl |
| 7 | 2-(2,3-dihydro-benzo[1,4]dioxinyl) | | $CH_2$ | $N(CH_3)$ | H | H |
| 8 | 2-(6-chloro-2,3-dihydro-benzo[1,4]dioxinyl) | S | $CH_2$ | NH | H | H |
| 9 | 2-(6-fluoro-2,3-dihydro-benzo[1,4]dioxinyl) | S | $CH_2$ | NH | H | H |
| 13 | 2-(5-fluoro-2,3-dihydro-benzo[1,4]dioxinyl) | S | $CH_2$ | NH | H | H |
| 14 | 2-(7-chloro-2,3-dihydro-benzo[1,4]dioxinyl) | S | $CH_2$ | NH | H | H |

TABLE 1-continued

Representative Compounds of Formula (I)

| ID No. | (R) | Stereo | (CH₂)ₐ | NR⁴ | R¹ | R² |
|---|---|---|---|---|---|---|
| 15 | 2-(6-chloro-benzo[1,3]dioxolyl) | | CH₂ | NH | H | H |
| 16 | 2-(2,3-dihydro-benzo[1,4]dioxinyl) | | CH₂CH₂ | NH | H | H |
| 19 | 2-(7-methyl-2,3-dihydro-benzo[1,4]dioxinyl) | S | CH₂ | NH | H | H |
| 20 | 2-(5-chloro-2,3-dihydro-benzo[1,4]dioxinyl) | S | CH₂ | NH | H | H |
| 22 | 2-(8-methoxy-2,3-dihydro-benzo[1,4]dioxinyl) | S | CH₂ | NH | H | H |
| 24 | 2-(6-bromo-2,3-dihydro-benzo[1,4]dioxinyl) | S | CH₂ | NH | H | H |
| 29 | 2-(6,7-dichloro-2,3-dihydro-benzo[1,4]dioxinyl) | S | CH₂ | NH | H | H |
| 30 | 2-(8-chloro-2,3-dihydro-benzo[1,4]dioxinyl) | S | CH₂ | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC₁-C₆alkylaminocarbonylC₁-C₆alkyl" substituent refers to a group of the formula

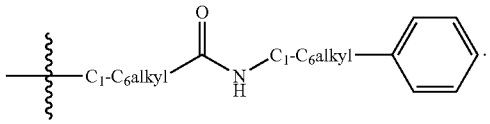

Abbreviations used in the specification, particularly the Schemes and Examples, are as follows DBU=2,3,4,6,7,8,9,10-Octahydropyrimido[1,2-a]azepine
DIPEA or DIEA=Diisopropylethylamine
DMF=N,N-Dimethylformamide
DMSO=Dimethylsulfoxide
EtOH=Ethanol
HPLC=High Pressure Liquid Chromatography
IPA=Isopropyl alcohol
MTBE=Methyl tert-Butyl Ether
TFA=Trifluoroacetic Acid
THF=Tetrahydrofuran As used herein, unless otherwise noted, the term "isolated form" shall mean that the compound is present in a form which is separate from any solid mixture with another compound(s), solvent system or biological environment. In an embodiment, the present invention is directed to a process wherein the compound of formula (I) is prepared in an isolated form. In an embodiment, the present invention is directed to a process wherein the compound of formula (I-S) is prepared in an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a process wherein the compound of formula (I) is prepared as a substantially pure compound. In an embodiment, the present invention is directed to a process wherein the compound of formula (I-S) is prepared as a substantially pure compound.

In another embodiment, the present invention is directed to a product prepared according to any of the processes described herein, wherein the product is substantially pure. In another embodiment, the present invention is directed to a product prepared according to any of the processes described herein, wherein the product is a substantially pure form of the compound of formula (I-S).

As used herein, unless otherwise noted, the term "substantially free of a corresponding salt form(s)" when used to describe the compound of formula (I) shall mean that mole percent of the corresponding salt form(s) in the isolated compound of formula (I) is less than about 5 mole percent, preferably less than about 2 mole percent, more preferably, less than about 0.5 mole percent, most preferably less than about 0.1 mole percent. In an embodiment, the present invention is directed to a process wherein the compound of formula (I) is prepared in a form which is substantially free of corresponding salt form(s). In an embodiment, the present invention is directed to a process wherein the compound of formula (I-S) is prepared in a form which is substantially free of corresponding salt form(s).

The compounds of formula (I) are benzo-fused sulfamide derivatives useful in the treatment and/or prevention of a number of disorders as disclosed in the following publications: US Patent Publication US2006-0041008 A1, published Feb. 23, 2006 discloses benzo-fused sulfamide derivatives useful for the treatment of epilepsy and related disorders; US Patent Publication 2007-0293440 A1, published Dec. 20, 2007 discloses co-therapy for the treatment of epilepsy and related disorder comprising administration of benzo-fused sulfamide derivatives and on or more anticonvulsants and/or anti-epileptic agents; US Patent Publication US Patent Publication 2009-0247616 A1, published Oct. 1, 2001 discloses the use of benzo-fused sulfamide derivatives for the treatment of anxiety and related disorders; US Patent Publication US2007-0155826 A1, published Jul. 5, 2007 discloses the use of benzo-fused sulfamide derivatives for the treatment of bipolar disorder and mania; US Patent Publication US2007-0155827 A1, published Jul. 5, 2007 discloses the use of benzo-fused sulfamide derivatives for the treatment of depression; US Patent Publication US2007-0155824 A1, published Jul. 5, 2007 discloses the use of benzo-fused sulfamide derivatives for the treatment of epileptogenesis; US Patent Publication US2007-0155821 A1, published Jul. 5, 2007 discloses the use of benzo-fused sulfamide derivatives for the treatment of glucose related disorders and for the treatment of lipid related disorders; US Patent Publication US2007-0191474 A1, published Aug. 16, 2007 discloses the use of benzo-fused sulfamide derivatives for the treatment of migraine; US Patent Publication US2007-0155823 A1, published Jul. 5, 2007 discloses the use of benzo-fused sulfamide derivatives for neuroprotection; US Patent Publication US2008-0027131 A1, published Jan. 31, 2008 discloses the use of benzo-fused sulfamide derivatives for the treatment of obesity; US Patent Publication US2007-0155822 A1, published Jul. 5, 2007 discloses the use of benzo-fused sulfamide derivatives for the treatment of pain; US Patent Publication US2007-0155825 A1, published Jul. 5, 2007 discloses the use of benzo-fused sulfamide derivatives for the treatment of substance abuse and/or addiction; which are herein incorporated by reference in their entirety.

In an embodiment, the present invention is directed to a method of treating and/or preventing the development of a disorder selected from the group consisting of (a) epilepsy and related disorders (preferably epilepsy, essential tremor or restless limb syndrome), (b) anxiety and related disorders, (c) bipolar disorder, (d) mania, (e) depression (preferably, major depressive disorder, unipolar depression or treatment refractory depression), (f) epileptogenesis, (g) glucose related disorders, (h) lipid related disorders, (i) migraine, (j) obesity, (k) pain, (l) substance abuse and/or addiction (preferably, alcohol abuse and/or addiction), or for (m) neuroprotection; comprising administering to a subject in need thereof a therapeutically effective amount of a product prepared according to any of the processes described herein. In another embodiment, the present invention is directed to a method for the treatment of epilepsy and related disorders, comprising administering to a subject in need thereof a therapeutically effective amount of a product prepared according to any of the processes described herein. In another embodiment, the present invention is directed to a method for the treatment of depression, preferably major depressive disorder, unipolar depression or treatment refractory depression; comprising administering to a subject in need thereof a therapeutically effective amount of a product prepared according to any of the processes described herein.

As used herein, the terms "anxiety and related disorders" and "anxiety or a related disorder" shall be defined to include anxiety and related disorders including generalized anxiety disorder, acute stress disorder, post traumatic stress disorder, obsessive-compulsive disorder, social phobia (also known as social anxiety disorder), specific phobia, panic disorder with or without agoraphobia, agoraphobia without a history of panic disorder, anxiety disorder due to general medical condition, substance abuse induced anxiety disorder and anxiety disorder not otherwise specified (as these conditions are described by their diagnostic criteria, as listed in the *Diagnostic and Statistical Manual of Mental Disorders*, 4$^{th}$ Edition, Text Revision, American Psychiatric Association, 2000, incorporated herein by reference). Preferably, the anxiety or related disorder is selected from the group consisting of generalized anxiety disorder, acute stress disorder, post traumatic stress disorder and obsessive-compulsive disorder. More preferably, the anxiety and related disorder is generalized anxiety disorder.

Bipolar disorder is psychiatric disorder characterized by unpredictable swings in mood from mania (or hypomania) to depression. As used herein, the term "bipolar disorder" shall include bipolar disorder I, bipolar disorder II, cyclothymic disorder and bipolar disorder not otherwise specified. Preferably, the bipolar disorder is characterized by depressive and manic (or hypomanic) phases, wherein the phases cycle. Preferably, the bipolar disorder is bipolar disorder I or bipolar disorder II.

As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders.

As used herein, unless otherwise noted the terms "cycling" or "bipolar cycling" shall refer to the alternation of mood between depressive and manic phases characteristic of bipolar disorders. Thus, the present invention includes methods for the stabilization of said cycling, including, but not limited to, decreasing the frequency of the cycling and/or decreasing the magnitude of the manic and/or depressive phases.

As used herein, the term "mania" shall include mania or a manic mood phase, regardless of underlying cause. As used herein, the term "bipolar mania" is intended to mean the mania associated with, characteristic of or symptomatic of a bipolar disorder. Thus, methods of treating bipolar mania of the present invention are directed to methods which treat the mania and/or manic phase of bipolar disorders.

As used herein, the term "depression" shall be defined to include major depressive disorder (including single episode and recurrent), unipolar depression, treatment-refractory depression, resistant depression, anxious depression and dysthymia (also referred to as dysthymic disorder). Further, the term "depression" shall encompass any major depressive disorder, dysthymic disorder and depressive disorder not otherwise specific as defined by their diagnostic criteria, as listed in the *Diagnostic and Statistical Manual of Mental Disorders*, 4$^{th}$ Edition, Text Revision, American Psychiatric Association, 2000. Preferably, the depression is major depressive disorder, unipolar depression, treatment-refractory depression, resistant depression or anxious depression. More preferably, the depression is major depressive disorder.

As used herein, unless otherwise noted, the terms "epilepsy and related disorders" or "epilepsy or related disorder" shall mean any disorder in which a subject (preferably a human adult, child or infant) experiences one or more seizures and/or tremors. Suitable examples include, but are not limited to, epilepsy (including, but not limited to, localization-related epilepsies, generalized epilepsies, epilepsies with both generalized and local seizures, and the like), seizures as a complication of a disease or condition (such as seizures associated with encephalopathy, phenylketonuria, juvenile Gaucher's disease, Lundborg's progressive myoclonic epilepsy, stroke, head trauma, stress, hormonal changes, drug use or withdrawal, alcohol use or withdrawal, sleep deprivation, and the like), essential tremor, restless limb syndrome, and the like. Preferably, the disorder is selected from epilepsy (regardless of type, underlying cause or origin), essential tremor or restless limb syndrome, more preferably, the disorder is epilepsy (regardless of type, underlying cause or origin) or essential tremor.

As used herein, the term "epileptogenesis" shall mean the biochemical, genetic, histological or other structural or functional processes or changes that make nervous tissue, including the central nervous system (CNS) susceptible to recurrent, spontaneous seizures. In addition, the term "epileptogenesis" is also used herein in a broader sense to refer to the changes and/or processes that contribute to the clinical progression observed in patients with epilepsy or other seizure disorder or an analogous seizure-related disorder including but not limited to; the worsening or progression of the disorder and it's symptoms or the development of "pharmacoresistance," in which the disorder becomes more difficult to treat as a result of neurobiological changes which result in reduced drug sensitivity or the recruitment by the process of epileptogenesis of non seizure prone nervous tissue. Furthermore the term "epileptogenesis" is used herein in the broadest possible sense to refer to the similar phenomena of progressive worsening over time of the signs and symptoms of apparently non-epileptic disorders, including psychiatric disorders the etiology of which appear to be seizure related.

Epileptogenesis is a Two Phase Process: "Phase 1 epileptogenesis" is the initiation of the epileptogenic process prior to the first epileptic seizure or symptom of an analogous seizure-related disorder, and is often the result of some kind of injury or trauma to the brain, i.e., stroke, disease (e.g., infection such as meningitis), or trauma, such as an accidental blow to the head or a surgical procedure performed on the brain. "Phase 2 epileptogenesis" refers to the process during which brain tissue that is already susceptible to epileptic seizures or seizure related phenomena of an analogous seizure-related disorder, becomes still more susceptible to seizures of increasing frequency and/or severity and/or becomes less responsive to treatment.

As used herein, the term "glucose related disorder" shall be defined as any disorder which is characterized by elevated glucose levels. Glucose related disorders include elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia and loss of muscle mass as a result of hyperglycemia (cachexia).

Treatment of glucose related disorders may comprise lowering glucose levels, improving glycemic control, decreasing insulin resistance and/or preventing the development of a glucose related disorder (for example preventing a patient suffering from impaired oral glucose tolerance or elevated glucose levels from developing Type II diabetes mellitus).

As used herein, the term "lipid related disorder" shall be defined as any disorder which is characterized by non-normal lipid levels. Lipid related disorders include elevated triglyceride levels, low HDL cholesterol and dyslipidemia, preferably elevated triglyceride levels or low HDL cholesterol levels. Treatment of lipid related disorder may comprise lowering triglycerides, elevating HDL cholesterol and/or improving the triglyceride/HDL ratio.

As used herein, the term "migraine" shall mean a chronic, episodic and debilitating clinical condition that is diagnosed by the presence of moderate to severe pulsating unilateral headaches lasting between 4 and 72 h, which includes migraine without aura and migraine with aura.

As used herein, "migraine without aura" shall mean at least five attacks fulfilling the following criteria: (a) the headache attack lasts 4-72 hours with the headache having at least two of the following features: unilateral location, pulsating quality, moderate or severe intensity with direct influence on activities of daily living, and aggravation by walking up stairs or similar routines; and (b) during the headache at least one of the following occurs: nausea and/or vomiting, and photophobia and phonophobia.

As used herein, "migraine with aura" shall mean at least two attacks accompanied by at least 3 of the 4 following features: (a) one or more fully reversible aura symptoms; (b) at least one aura symptom which develops gradually over more than four minutes or two or more symptoms which occur in succession; (c) no aura symptom which lasts more than 60 minutes; (d) a headache occurs prior to, simultaneously with or following the aura, with a free interval between aura and headache of less than about 60 minutes.

As used herein, the term "prevention" shall include the prevention of migraine attacks (headaches), a decrease in the frequency of migraine attacks (headaches), a decrease in the severity of migraine attacks (headaches) and/or a decrease in the duration of migraine attacks (headaches).

As used herein, the term "obesity" shall be defined as a body mass index (BMI) of greater than or equal to about 25, preferably a BMI of greater than or equal to about 30. Thus as used herein, the term "obesity" shall include both overweight and clinically obese subjects/patients.

As used herein, the term "pain" shall be defined to include acute, chronic, inflammatory and neuropathic pain (preferably diabetic neuropathy). Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

In an embodiment of the present invention, is a method for the treatment of pain, wherein the pain is acute pain. In another embodiment of the present invention, is a method for the treatment of pain, wherein the pain is chronic pain. In another embodiment of the present invention, is a method for the treatment of pain, wherein the pain is neuropathic pain, more preferably diabetic neuropathy. In yet another embodiment of the present invention, is a method for the treatment of pain, wherein the pain is inflammatory pain.

In an embodiment, the pain is selected from the group consisting of osteoarthritis, rheumatoid arthritis, fibromyalgia, headache, toothache, burn, sunburn, animal bite (such as dog bite, cat bite, snake bite, spider bite, insect sting, and the like), neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, labor, childbirth, menstrual cramps, cancer, back pain, lower back pain and carpal tunnel syndrome pain.

Acute pain includes pain caused by acute injury, trauma, illness or surgery (for example, open-chest surgery (including open-heart or bypass surgery)). Acute pain also includes, and is not limited to, headache, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, headache, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

Neuropathic pain includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathetic dystrophy, phantom limb syndrome and other chronic and debilitating condition-associated pain syndromes.

As used herein, the term "treatment of substance abuse" shall include treatment of substance abuse or addiction, including but not limited to the treatment of carvings, withdrawal, and other symptoms of addiction or abuse. As used herein, unless otherwise noted the term "substance" when referring to substances of abuse and/or addiction shall include any legal or illegal substance to which a subject or patient may develop an addiction. Suitable examples include, but are not limited to alcohol, cocaine, heroine, methamphetamine, ketamine, Ecstacy, nicotine, oxycontin/oxycodone, codeine, morphine, and the like.

As used herein, the term "neuroprotection" shall mean the protecting neurons in the brain, central nervous system or peripheral nervous system (preferably in the brain or spinal cord) from death and/or damage. Preferably, the neurons are protected from death or damage caused by oxidative stress, for example oxygen radicals.

"Acute neurodegenerative disorders" included within the methods of the present invention include, but are not limited, to various types of acute neurodegenerative disorders associated with neuron death or damage including cerebrovascular insufficiency, focal brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome. Preferably, the acute neurodegenerative disorder is a result of stroke, acute ischemic injury, head injury or spinal injury.

"Chronic neurodegenerative disorders" included within the methods of the present invention included, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Straussler-Scheinker disease, Kuru and fatal familial insomnia). Preferably, the chronic neurodegenerative disorder is selected from Alzheimer's disease, Parkinson's disease, multiple sclerosis or cerebral palsy, Other disorders which manifest neuron death or damage and as such are intended to be included within the methods of the present invention include dementias, regardless of underlying etiology, including age-related dementia and other dementias and conditions with memory loss including dementia associated with Alzheimer's disease, vascular dementia, diffuse white matter disease (Binswanger's disease), dementia of endocrine or metabolic origin, dementia of head trauma and diffuse brain damage, dementia pugilistica and frontal lobe dementia.

Also included within the present invention are methods of neuroprotection (i.e. methods for the prevention of neuron death and/or damage) following injury to the brain, central nervous system or peripheral nervous system, wherein the injury resulting from chemical, toxic, infectious, radiation and/or traumatic injury. Preferably, the methods of the present invention are directed to preventing neuron death or damage following brain, head and/or spinal cord trauma or injury, regardless of cause.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "preventing", "prevention", and the like, shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee = ([\alpha-obs]/[\alpha-max]) \times 100.$$

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, 1,1-dichloroethane, dichloromethane, MTBE, toluene, acetone, and the like.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention is directed to a process for the preparation of compounds of formula (I), as outlined in more detail in Scheme 1, below.

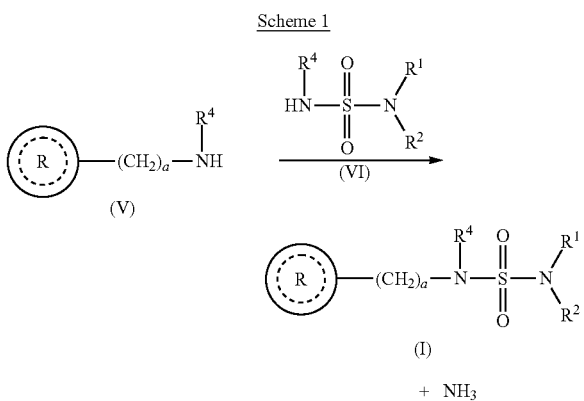

Accordingly, a suitably substituted compound of formula (V), a known compound or compound prepared according to known methods is reacted with a suitably substituted compound of formula (VI), a known compound or compound prepared by known methods;

wherein the compound of formula (VI) is preferably present in an amount in the range of from about 1.0 to about 5.0 molar equivalents (relative to the moles of the compound of formula (V)), more preferably in an amount in the range of from about 2.0 to about 4.0 molar equivalents, more preferably, in an amount in the range of from about 3.0 to about 3.5 molar equivalents, more preferably, in an amount of about 3.3 molar equivalents;

preferably, in the presence of a suitably selected buffer system; for example, in a mixture of a suitably selected acid such as HCl, HBr, $H_2SO_4$, and the like, preferably HCl; and a suitably selected organic base such as DIPEA, DBU, pyridine, and the like; preferably DIPEA;

wherein the acid is preferably present in an amount in the range of from about 1.0 to about 1.5 molar equivalents (relative to the moles of the compound of formula (V)), more preferably in an amount of about 1.2 molar equivalents; and wherein the organic base is preferably present in an amount in the range of from about 1.0 to about 1.5 molar equivalents (relative to the moles of the compound of formula (V)), more preferably in an amount of about 1.3 molar equivalents in water or an aqueous solvent system; wherein the aqueous solvent system is a mixture of water and a suitably selected solvent such as an alcohol, such as IPA, EtOH, n-propanol, and the like; preferably, in a mixture of water and IPA; more preferably, in an 8:1 mixture of water:IPA (i.e. 11% mixture);

at reflux temperature of less than/or equal to about 90° C., more preferably at reflux temperature of about 85° C. to about 90° C.; preferably, for a period of time in the range of from about 2 to about 6 hours, more preferably for about 4 hours; to yield the corresponding compound of formula (I); and ammonia as a by-product.

Preferably, the compound of formula (V) is reacted with the compound of formula (VI) under conditions where ammonia (which is formed as a by-product of the reaction) is removed throughout the time of the reaction (for example, by distillation), to drive the reaction to preparation of the desired product, the compound of formula (I).

Preferably, the compound of formula (I) is further isolated and/or purified according to known methods. In an example, the compound of formula (I) is isolated by filtration. In another example, the compound of formula (I) is purified by recrystallization.

In an embodiment, the present invention is directed to a process for the preparation of compounds of formula (I-S), as outlined in more detail in Scheme 2, below.

Scheme 2

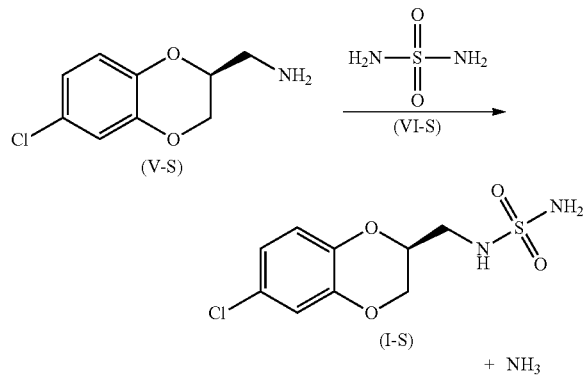

Accordingly, a suitably substituted compound of formula (V-S), a known compound or compound prepared according to known methods is reacted with a suitably substituted compound of formula (VI-S), a known compound or compound prepared by known methods;

wherein the compound of formula (VI-S) is preferably present in an amount in the range of from about 1.0 to about 5.0 molar equivalents (relative to the moles of the compound of formula (V-S)), more preferably in an amount in the range of from about 2.0 to about 4.0 molar equivalents, more preferably, in an amount in the range of from about 3.0 to about 3.5 molar equivalents, more preferably, in an amount of about 3.3 molar equivalents;

preferably, in the presence of a suitably selected buffer system; for example, in a mixture of a suitably selected acid such as HCl, HBr, $H_2SO_4$, and the like, preferably HCl; and a suitably selected organic base such as DIPEA, DBU, pyridine, and the like; preferably DIPEA;

wherein the acid is preferably present in an amount in the range of from about 1.0 to about 1.5 molar equivalents (relative to the moles of the compound of formula (V-S)), more preferably in an amount of about 1.2 molar equivalents; and wherein the organic base is preferably present in an amount in the range of from about 1.0 to about 1.5 molar equivalents (relative to the moles of the compound of formula (V-S)), more preferably in an amount of about 1.3 molar equivalents in water or an aqueous solvent system; wherein the aqueous solvent system is a mixture of water and a suitably selected solvent such as an alcohol, such as IPA, EtOH, n-propanol, and the like; preferably, in a mixture of water and IPA; more preferably, in an 8:1 mixture of water:IPA (i.e. 11% mixture);

at reflux temperature of less than/or equal to about 90° C., more preferably at reflux temperature of about 85° C. to about 90° C.; preferably, for a period of time in the range of from about 2 to about 6 hours, more preferably for about 4 hours; to yield the corresponding compound of formula (I-S); and ammonia as a by-product.

Preferably, the compound of formula (V-S) is reacted with the compound of formula (VI-S) under conditions, where ammonia (which is formed as a by-product of the reaction) is removed throughout the time of the reaction (for example, by distillation), to drive the reaction to preparation of the desired product, the compound of formula (I-S).

Preferably, the compound of formula (I-S) is further isolated and/or purified according to known methods. In an example, the compound of formula (I-S) is isolated by filtration. In another example, the compound of formula (I-S) is purified by recrystallization.

Preferably, the compound of formula (I-S) is further isolated according to known methods, for example by filtration or crystallization. Preferably, the compound of formula (I-S) is further purified according to known methods, for example by crystallization or recrystallization, with optional seeding (for example as described in example 2 which follows herein).

The present invention further comprises pharmaceutical compositions containing one or more compounds of formula (I) prepared according to the process as described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1,000 mg or any amount or range therein, and may be given at a dosage of from about 0.01 to about 100 mg/kg/day, or any amount or range therein, preferably, from about 0.1 to about 50.0 mg/kg of body weight per day, or any amount or range therein; preferably, from about 0.1 to about 15.0 mg/kg of body weight per day, or any range therein, preferably from about 0.5 to about 7.5 mg/kg of body weight per day, or any amount or range therein. The dosages, however, may be varied depending upon the requirement of the patients, the severity of the condition being treated and the compound being employed. The use of either daily administration or postperiodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating epilepsy and related disorders described in the present invention may also be carried out using a pharmaceutical composition comprising any of the compounds as defined herein and a pharmaceutically acceptable carrier. The pharmaceutical composition may contain between about 0.01 mg and 1,000 mg of the compound, or any amount or range therein; preferably from about 10 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I), prepared according to the process as described herein, as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of anxiety and related disorders; bipolar depression and mania; depression; epilepsy and related disorders; epileptogenesis; glucose related disorders; lipid related disorders; migraine; obesity; pain; substance abuse or neuroprotection is required.

The daily dosage of the products may be varied over a wide range from 1.0 to 10,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range may be from about 0.1 to about 50.0 mg/kg of body weight per day, or any amount or range therein. In another example, the range may be from about 0.1 to about 15.0 mg/kg of body weight per day, or any range therein. In yet another example, the range may be from about 0.5 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Examples 1 and 2 describe recipes/procedures for the synthesis of the titled compound(s). One or more batches of the said compound(s) were prepared according to the recipes/ procedures as described below. Wherein the recipe/procedure lists a range for the time, temperature or other reaction parameter, the procedure was applied such that said time, temperature or other reaction parameter(s) was maintained within the listed range.

EXAMPLE 1

Synthesis of the Compound of Formula (I-S) in 1,4-Dioxane

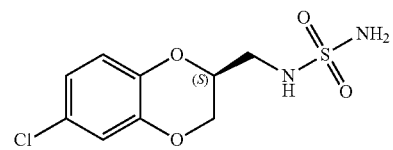

To (2S)-6-chloro-2,3-dihydro-1,4-benzodioxin-2-methanamine (1.60 g, 8 mmol) and sulfamide (3.08 g, 32 mmol) was added 1,4-dioxane (20 g) and the resulting mixture was stirred at about 100° C. for 36 h, then cooled to a temperature in the range of 30° C. to 50° C. The solvent was then evaporated to yield a residue. Water (10 g) and toluene (10 g) were added to the residue and the resulting mixture was stirred at a temperature in the range of 70° C. to 85° C. The resulting phases were separated and the organic layer was washed with water (5 g) (at the reaction temperature/without prior cooling). The toluene phase was then separated and the solvent evaporated, whereupon the title compound was observed to crystallize.

EXAMPLE 2

Synthesis of the Compound of Formula (I-5) in Water:IPA

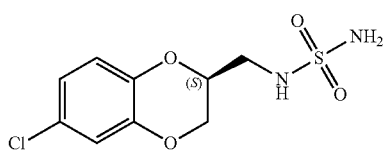

To (2S)-6-chloro-2,3-dihydro-1,4-benzodioxin-2-methanamine (15.0 g, 75 mmol) and sulfamide (23.8 g, 248 mmol) was added water (120 g) at a temperature in the range of 20° C. to 30° C., followed by addition of isopropanol (15.0 g). To the resulting suspension was then added hydrochloric acid (37%, 7.4 g, 75 mmol). The resulting mixture was then heated to 80-85° C. and N,N-diisopropylethylamine (12.6 g, 97.5 mmol) was added, at this temperature over about 30 to 50 minutes. The resulting mixture was refluxed for an additional 30 to 60 minutes, distilling off about 11 to 13 g of solvent. After cooling the resulting mixture to a temperature in the range of 60° C. to 70° C., hydrochloric acid (37%) was added until a pH in the range of 1.4 to 2.2 was reached. The resulting mixture was cooled to a temperature in the range of 45° C. to 25° C. and seeded with the desired product (40 mg), whereupon the emulsion was observed to change to a suspension. The suspension was cooled to a temperature in the range of 15° C. to 25° C. and stirred at this temperature for 1.5 to 3 h. The title compound was isolated by filtration, washed with water (120 g) and dried at a temperature in the range of 50° C. to 60° C. under vacuum.

EXAMPLE 3

Solvent Comparison

The following reaction

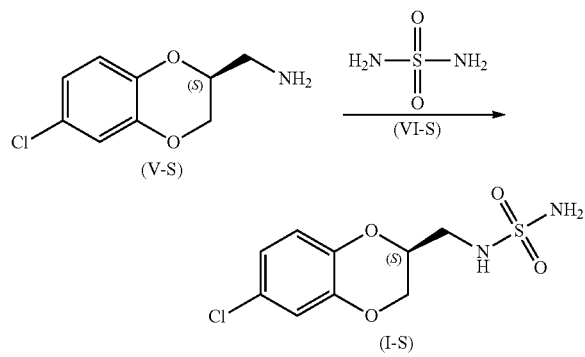

was run once in 1,4-dioxane, once in an aqueous solvent system of 8:1 (11%) water:IPA mixture, and several times in water. Table 3 below lists representative reaction times, yields and purity for the different solvent systems. In the table below, the notation "(max)" in the "Water" column indicates that the listed results are the best results obtained from analysis of several water solvent condition experiments.

TABLE 3

| Solvent Comparison Product Results | | | |
|---|---|---|---|
| Solvent | 1,4-dioxane | Water | 8:1 Water:IPA |
| Reaction Time | 53 hours | 17 hours | 4 hours |
| % Conversion | 89% | 73% (max) | 97.5% |
| Yield (corrected) | 81% | 65% (max) | 89% |
| Volume Yield | 6.3% | 7.1% (max) | 9.8% |
| HPLC-purity | 98% | 95% | 98% |
| HPLC-assay | 92% | 93% | 95% |

EXAMPLE 4

Recrystallization of Compound of Formula (I-S) from Isopropanol/n-Heptane

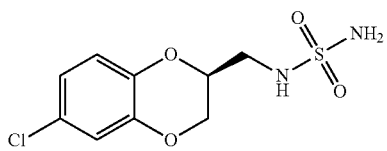 [SMILES: NS(=O)(=O)NC[C@H]1COc2cc(Cl)ccc2O1]

The following describes a batch recipe or procedure, which was followed for the recrystallization of the compound of formula (I-S). Wherein the recipe/procedure lists a range for the time, temperature or other reaction parameter, the procedure was applied such that said time, temperature or other reaction parameter(s) were maintained within the listed range.

Two portions of the compound of formula (I-S) (prepared as described above) (3.80 kg, 13.6 mol) and (5.50 kg, 19.8 mol) were added to a reactor vessel. Isopropanol (15.5 kg) and n-heptane (15.4 kg) were then added. The resulting suspension was heated to reflux (internal temperature of 75° C.) and stirred continuously for 15-25 minutes. The internal temperature was adjusted to 70-72° C. and the resulting solution filtered into a second reactor. The filter pad was rinsed with hot (74° C.) isopropanol (1.7 kg) and n-heptane (1.7 kg). The internal temperature of the filtrate was adjusted to about 50-54° C. and the solution seeded with Polymorph VI of the compound of formula (I-S) (0.02 kg) (Polymorph VI of the compound of formula (I-S), and a method for the preparation of Polymorph VI of the compound of formula (I-S) are described in published US Patent Application US-2009-0318544 A1, published Dec. 24, 2009). The resulting mixture was stirred at this temperature for 45-50 minutes. n-Heptane (14.4 kg) was then added over about 10-30 minutes. The resulting suspension was cooled to 3° C. over 50 min and the resulting mixture stirred for an additional 60 to 180 minutes. The resulting suspension was centrifuged, the wet filter cake washed with n-heptane (18.7 kg) and the resulting wet solid (8.6 kg, 86%) dried under vacuum at 50-60° C. to yield the title compound as a crystalline white solid.

Purity by HPLC: 99.95 area %

EXAMPLE 5

HPLC Method for Measuring Process Impurities

The following HPLC-method was used for the assay determination of the synthesis process impurities, using an Agilent HP1100 equivalent; DAD detector or equivalent and Waters Empower 2 or equivalent. Instrument parameters were as follows:

Runtime: 39 minutes
Equilibration time: 6 minutes
Flow rate: 1.2 mL/min
Injection volume: 10 µL, Injection with needle wash; Wash solution: Solvent Supelcosil, Ascentis RP-Amide, 3 µm, 4.6×150 mm
Column: (Supplier: Supelco, Product No. 565322)
Mobile Phase A 1 mM Ammonium Acetate and 0.01% Acetic Acid in Water/Acetonitrile (95:5, v/v)
Mobile Phase B 1 mM Ammonium acetate and 0.01% Acetic Acid in Acetonitrile/Water (95:5, v/v)
Gradient:

| Time | % A | % B |
|------|-----|-----|
| 0    | 90  | 10  |
| 25   | 55  | 45  |
| 35   | 20  | 80  |
| 38   | 20  | 80  |
| 39   | 90  | 10  |

Column Temperature: 55° C.
Autosampler Temperature: ambient
Detection: UV, 235 nm (bandwidth 10 nm)

The reagents used were as follows: Water Milli-Q or equivalent; Ammonium Acetate, Scharlau HPLC grade (Art. No. AM0255) or equivalent; Acetic Acid 100%, Merck p.a. (Art. No. 1.00063.1000) or equivalent; and Acetonitrile, Scharlau gradient HPLC grade (Art. No. AC0331) or equivalent.

Mobile Phase A was prepared by dissolving ammonium acetate (77.08 mg) in water (950 mL) in a 1 L contained and then adding glacial acetic acid (0.1 mL) and acetonitrile (50 mL), then mixing well and degassing the resulting mixture. Mobile Phase B was prepared by dissolving ammonium acetate (77.08 mg) in water (950 mL) in a 1 L contained and then adding glacial acetic acid (0.1 mL) and acetonitrile (950 mL), then mixing well and degassing the resulting mixture.

The solvent used was a mixture of acetonitrile/water 1:1, (v:v). Standard stock solution was prepared by weighing compound of formula (I-S) (about 50 mg±5 mg) into a 50-mL volumetric flask. The material was then dissolved by filling the flask to the mark with solvent and mixing well. Sensitivity solution (0.05%) was prepared by pipetting standard solution (2.0 mL) into a 100 mL volumetric flask and then filling to the mark with solvent (5% solution). The diluted solution (2.5 mL) was then pipette into a 100 mL volumetric flask, which was then filled to the mark with solvent to yield the sensitivity solution at 0.05%. Specificity solution was prepared by weighing sample material (50.0 mg±2.0 mg) into a 50-mL volumetric flask. To the flask was then added a solution of the impurity to be tested (0.5 mL of a 0.1 mg/mL solution of impurity). The material was then dissolved by filling the flask to the mark and mixing well. Sample solution was prepared by weighing sample substance 50.0 mg±2.0 mg) into a 50-mL volumetric flask. The material was then dissolved by filling the flask to the mark with solvent and mixing well.

Typical retention times for the various impurities were as listed in Table 4, below.

TABLE 4

Impurity Retention Times

| Compound/Impurity | Retention Time (min) | Relative Retention Time |
|---|---|---|
| (7-chloro-2,3-dihydro-1,4-benzodioxin-2-yl)methanamine | 5.0 | 0.33 |
| N-[(7-chloro-2,3-dihydro-1,4-benzodioxin-2-yl)methyl]sulfamic acid | 10.5 | 0.70 |
| N-[(7-chloro-2,3-dihydro-1,4-benzodioxin-2-yl)methyl]imidodisulfuramide | 11.9 | 0.80 |
| bis-sulfamide dimer | 32.4 | 2.17 |

Purity in area % was calculated according to standard methods.

EXAMPLE 6

Determination of Product Impurity Profile

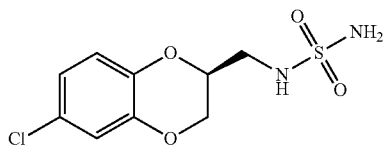 [SMILES: NS(=O)(=O)NC[C@H]1COc2cc(Cl)ccc2O1]

A number of batches of the compound of formula (I-S) were prepared according to the procedure of the present invention and then re-crystallized from a mixture of isopropanol and n-heptane, as described in Example 4 above.

Samples of material isolated prior to re-crystallization (labeled "Crude" below) and samples of material isolated after re-crystallization (labeled "Recryst" below) were analyzed by HPL, applying the method as described in Example 5, above, to determine the amount and identity of any impurities. Tables 5a and 5b below, lists the measured impurities (in area %) for said samples. The notation "nd" indicates that the impurity was not detected. One skilled in the art will recognize that such a designation indicates that the impurity was either absent, or, if present, was present in an amount below the detection limit of the HPLC method.

TABLE 5a

| Impurity Profile "Crude" | | | | | |
|---|---|---|---|---|---|
| Impurity | Sample A | Sample B | Sample C | Sample D | Sample E |
| (structure) | nd | nd | 0.20 | 0.03 | 0.37 |
| (structure) | nd | 0.03 | 0.08 | 0.02 | 0.12 |
| (structure) | 0.02 | 0.02 | 0.23 | 0.04 | 0.41 |
| (structure) | nd | nd | 0.22 | 0.16 | 0.17 |

TABLE 5b

| Impurity Profile "Recryst" | | | |
|---|---|---|---|
| Impurity | Sample F | Sample G | sample H |
| (structure) | nd | 0.05 | 0.17 |
| (structure) | nd | nd | 0.04 |

TABLE 5b-continued

Impurity Profile "Recryst"

| Impurity | Sample F | Sample G | sample H |
|---|---|---|---|
| 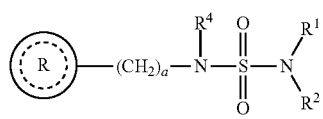 | nd | 0.09 | 0.31 |
| 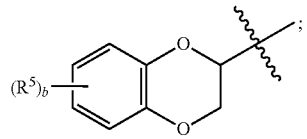 | nd | 0.08 | 0.05 |

FORMULATION EXAMPLE 1

Oral Dosage Formulation-Prophetic Example

As a specific embodiment of an oral composition, 100 mg of the compound prepared as in Example 2 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

wherein
R$^1$ and R$^2$ are each independently selected from the group consisting of hydrogen and lower alkyl;
R$^4$ is selected from the group consisting of hydrogen and lower alkyl;
a is an integer from 1 to 2;

is (R$^5$)$_b$ —[benzodioxine structure];

wherein b is an integer from 0 to 4; and wherein each R$^5$ is independently selected from the group consisting of halogen and lower alkyl;
and pharmaceutically acceptable salts thereof;

comprising

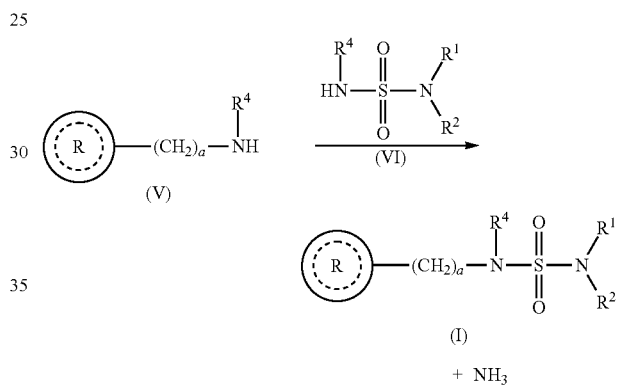

+ NH$_3$ reacting a compound of formula (V-S) with a compound of formula (VI-S); in the presence of a acid organic base buffer system in water or an aqueous solvent system; at reflux temperature; to yield the corresponding compound of formula (I-S) and ammonia.

2. A process as in claim 1, wherein R$^1$ is hydrogen, R$^2$ is hydrogen, R$^4$ is hydrogen, a is 1 and

is 2-(6-chloro-2,3-dihydro-benzo[1,4]dioxinyl).

3. A process for the preparation of a compound of formula (I-S)

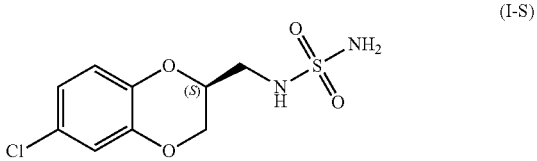

or a pharmaceutically acceptable salt thereof; comprising

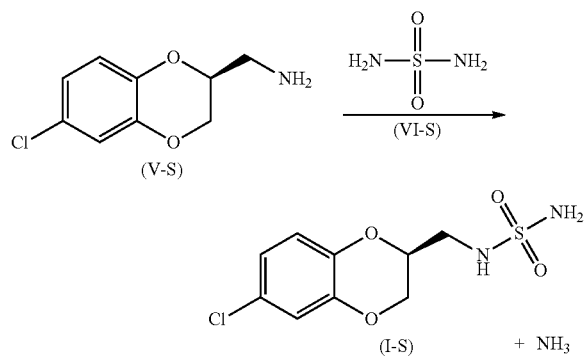

reacting a compound of formula (V-S) with a compound of formula (VI-S); in the presence of a buffer system; in water or an aqueous solvent system; at reflux temperature; to yield the corresponding compound of formula (I-S) and ammonia.

4. A process as in claim 3, wherein the compound of formula (VI-S) is present in an amount of about 3.3 molar equivalents.

5. A process as in claim 3, wherein the water or aqueous solvent system is water or a mixture of water and isopropyl alcohol.

6. A process as in claim 5, wherein the mixture of water and isopropyl alcohol is an 8:1 mixture.

7. A process as in claim 3, wherein the buffer system is a mixture of 1.2 molar equivalents of HCl and 1.3 molar equivalents of DIPEA.

8. A process as in claim 3, wherein the reflux temperature is in the range of about 85° C. to about 90° C.

9. A process as in claim 3, further comprising distillation of the ammonia formed in the reaction of the compound of formula (V-S) with the compound of formula (VI-S).

* * * * *